United States Patent

Robinson et al.

Patent Number: 5,668,196
Date of Patent: Sep. 16, 1997

[54] 3-AMIDO-TRIIODOPHENYL ESTERS AS X-RAY CONTRAST AGENTS

[75] Inventors: Shaugnessy Robinson, Westerly, R.I.; Edward R. Bacon, Audubon; Kurt A. Josef, Wayne, both of Pa.

[73] Assignee: NanoSystems LLC, Collegeville, Pa.

[21] Appl. No.: 677,709

[22] Filed: Jul. 10, 1996

Related U.S. Application Data

[60] Provisional application No. 60/002088, Aug. 10, 1995

[51] Int. Cl.$^6$ .................... A61K 49/00; G01N 31/00; G01N 33/48

[52] U.S. Cl. .................... 424/9.451; 424/9.4; 424/9.44; 424/9.45

[58] Field of Search ............... 424/1.11, 1.65, 424/9.1, 9.4, 9.44, 9.45, 9.451

[56] References Cited

U.S. PATENT DOCUMENTS

| | | | |
|---|---|---|---|
| 3,701,771 | 10/1972 | Almen et al. | 424/9.4 |
| 4,225,577 | 9/1980 | Tilly et al. | 424/1.11 |
| 4,314,055 | 2/1982 | Hoey et al. | 536/53 |
| 4,584,401 | 4/1986 | Sovak et al. | 564/153 |
| 5,191,119 | 3/1993 | Sovak et al. | 564/153 |

*Primary Examiner*—John Kight
*Assistant Examiner*—Dameron L. Jones
*Attorney, Agent, or Firm*—Rudman & Balogh

[57] ABSTRACT

This invention relates to methods of x-ray diagnostic imaging the blood pool, liver, spleen and/or lymph system of a mammal comprising administering a contrast effective amount of a contrast agent having the structure:

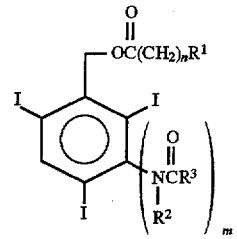

wherein:
n is 0 to 12
m is 1 or 2

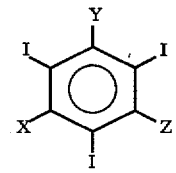

$R^1$ is
X and Z are independently H or $NR^2COR^3$
Y is $CO_2$, $CH_2O$, O or NH and
$R^2$ and $R^3$ are independently H, alkyl having from 1 to 12 carbon atoms or aryl having from 6 to 11 carbon atoms, This invention further relates to novel contrast agents having the above structure wherein $R^1$ is

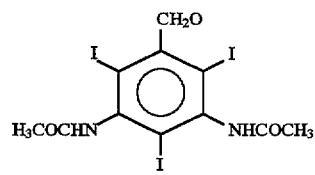

$R^2$ is H and $R^3$ is $CH_3$ to x-ray contrast compositions comprising such agents, and to method of x-ray diagnostic imaging utilizing such agents.

13 Claims, No Drawings

3-AMIDO-TRIIODOPHENYL ESTERS AS X-RAY CONTRAST AGENTS

This application claims the benefit under 35 USC 119(e) of Provisional Application No. 60/002,088 filed Aug. 10, 1995.

FIELD OF INVENTION

This invention relates to methods of x-ray diagnostic imaging the blood pool, liver, spleen and/or lymph system of a mammal employing particulate compounds as a contrast agent, and to certain novel compounds useful as contrast agents in x-ray contrast compositions and methods of diagnostic imaging.

BACKGROUND OF THE INVENTION

X-ray imaging is a well known and extremely valuable tool for the early detection and diagnosis of various disease states in the human body. The use of contrast agents for image enhancement in medical x-ray imaging procedures is widespread. An excellent background on iodinated and other contrast agents for medical imaging is provided by D. P. Swanson, et al, *Pharmaceuticals in Medical Imaging*, 1990, MacMillan Publishing Company.

Great Britain Patent No. 889339 describes an x-ray contrast composition comprising an iodinated benzoic acid derivative and a non-toxic carrier. The compounds collect in the gall bladder.

U.S. Pat. No. 3,097,228 describes derivatives of 2,4,6-triiodobenzoyloxyalkanoic acids having the structure

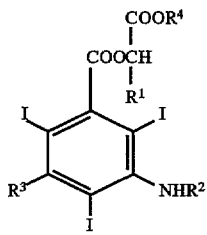

wherein $R^1$ is H or lower alkyl; $R^2$ is H or lower akanoyl; $R^3$ is H or lower alkanoylamino and $R^4$ is lower alkyl. The agents are useful as x-ray contrast agents for visualizing the gall bladder (cholecystography) when administered orally, in the free acid form or in the form of a non-toxic salt, or intravenously, in the form of a water soluble, non-toxic salt. Example 15 therein describes ethyl 2-(3,5-diacetamido-2,4,6-triiodobenzoyloxy) hexanoate, i.e.,

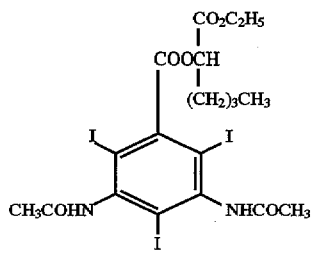

Bacon et al, commonly assigned U.S. Pat. No. 5,322,679 issued 21 Jun. 1994 describes nanoparticulate iodinated aroyloxy esters which are useful as contrast agents in x-ray imaging compositions and methods. However, all of the compounds described by Bacon et al feature an ester group linked through a $C_2$ or higher alkylene group to another ester group on an iodinated aromatic ring.

U.S. Pat. No. 3,128,301 by Larsen et al describes x-ray contrast agents having the structure:

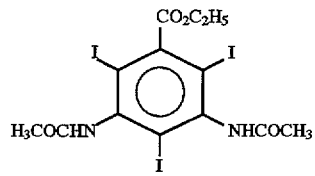

which contains a carboxylic ester group.

EP-A-498,482 describes nanoparticulate x-ray contrast compositions which have proven to be extremely useful in medical imaging. The compositions comprise particles of an organic x-ray contrast agent and a surface modifier adsorbed on the surface thereof and have an effective average particle size of less than 400 nm. The agents can be delivered to a specific tissue or fluid site, e.g., the blood pool, liver, spleen, kidney or lymph nodes. Example 8, therein describes a formulation comprising ethyl 2-(3,5-bis(acetylamino)-2,4,6-triiodobenzoyloxy) butyrate, i.e.,

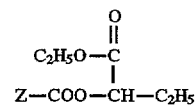

wherein (Z)—COO is the residue of diatrizoic acid.

However, it has been discovered that ethyl 2-(3,5-bis (acetylamino)-2,4,6-triiodobenzoyloxy) butyrate exhibits multiple crystal forms, i.e., polymorphs, e.g., when recrystallized from various solvents. The reasons that this behavior are not completely understood but, in any event, multiple crystal forms are disadvantageous for a variety of reasons. For example, the presence of multiple crystal forms renders scale up problematic due to the lack of reproducibility of the results obtained, including, e.g., in chemical manufacturing and in the milling process. Additionally, it has been found the nanoparticulate formulations of ethyl 2-(3,5-bis (acetylamino)-2,4,6-triiodobenzoyloxy) butyrate do not exhibit good stability during autoclaving, i.e., conventional heat sterilization.

Consequently, it would be highly desirable to provide a poorly soluble x-ray contrast agent having the advantages of ethyl 2-(3,5-bis(acetylamino)-2,4,6-triiodobenzoyloxy) butyrate but which exhibits a consistent and reproducible crystal morphology, optimum hydrolysis, solubility and a high melting point is amenable to reproducible scale up and can be successfully heat sterilized by autoclaving to produce a stable and less toxic material.

SUMMARY OF THE INVENTION

I have discovered that certain compounds exhibit reproducibly consistent crystal morphology during manufacture and purification, optimum hydrolysis, solubility and a high melting point and thus are particularly amenable to reproduce as particulate contrast agents for use in methods of x-ray diagnostic imaging the blood pool, liver, spleen and lymphatic system of a mammal. In a composition of matter aspect, I have discovered and synthesized novel compounds which are useful as contrast agents in x-ray diagnostic imaging compositions and methods.

More specifically, in accordance with this invention, there is provided a method of medical x-ray diagnostic imaging which comprises administering to the blood pool, liver, spleen or lymph system of a mammal a contrast-effective amount of a particulate contrast agent (3-amido-triiodophenyl esters) having structure 1:

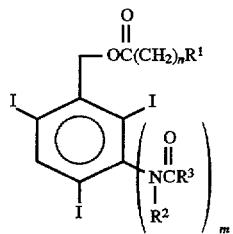

wherein:

n is 0 to 12 m is 1 or 2.

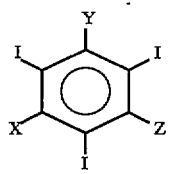

$R^1$ is

X and Z are independently H or $NR^2COR^3$

Y is $CO_2$, $CH_2O$, O or NH $R^2$ and $R^3$ are independently H, alkyl having from 1 to 12 carbon atoms or aryl having from 6 to 11 carbon atoms, In another aspect, there are provided novel compounds having structure 1 above wherein $R^1$ is

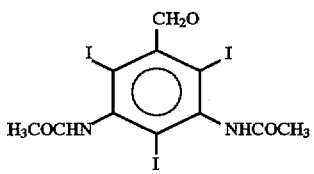

$R^2$ is H and $R^3$ is $CH_3$. This invention further provides an x-ray contrast composition comprising such novel compounds and a method for medical x-ray diagnostic imaging which comprises administering to a mammal an effective contrast-producing amount of the above-described x-ray contrast composition.

It is an advantageous feature of this invention that methods of x-ray diagnostic imaging the blood pool, liver, spleen and lymphatic system are provided employing an x-ray contrast composition featuring a compound which exhibits a consistent crystal morphology during purification and thus is particularly amenable to reproducible scale up and has optimum hydrolysis, solubility and a high melting point.

It is another advantageous feature of this invention that x-ray contrast compositions are provided for blood pool, liver, spleen and lymphatic system imaging which exhibit improved visualization.

Still another advantageous feature of this invention is that novel compounds are provided which find particular utility as particulate x-ray contrast agents.

DESCRIPTION OF PREFERRED EMBODIMENTS

In structure 1 above, n is 0 to 12, m is 1 or 2 and $R^1$ is

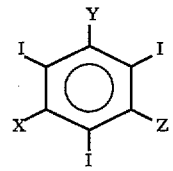

X and Z are independently either H or $NR^2COR^3$ and Y is $CO_2$, $CH_2O$, O or NH.

$R^2$ and $R^3$ are independently H, alkyl or aryl.

The alkyl group can be either branched or straight chained. The alkyl group preferably contains from 1 to 12 carbon atoms such as methyl, ethyl, isopropyl, butyl, hexyl, decyl and the like. Preferably $R^2$ is H and $R^3$ is $CH_3$.

The aryl group preferably contains from 6 to 11 carbon atoms such as phenyl and the like.

The preferred 3-amido-triiodophenyl ester in accordance with this invention has the structure:

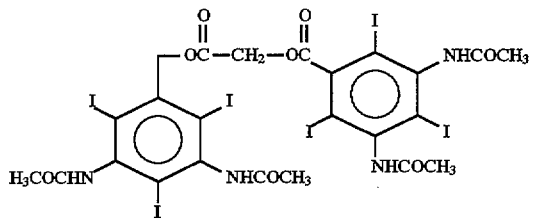

The compound of this invention can be prepared by reacting a compound having the structure

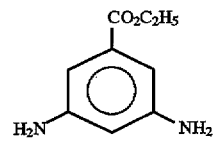

with a nitride to form a compound having the structure

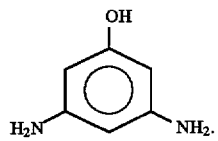

This compound is reacted with 1) $Ac_2O$ or 2) $OH^-$ to form a compound having the structure

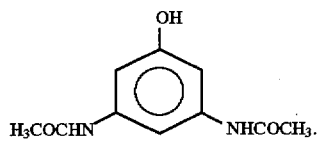

This compound, in turn, is mixed with $NaICl_2$ to form a compound having the structure

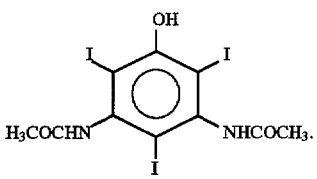

This compound is then mixed with

to form a compound having the structure:

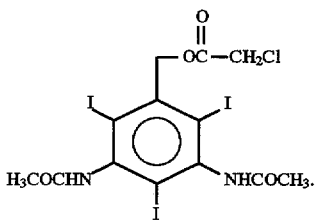

The above product is then reacted with diatrizoic acid, $K_2CO_3$ and DMF at a temperature of 30°–80° C. to form the preferred compound having the structure:

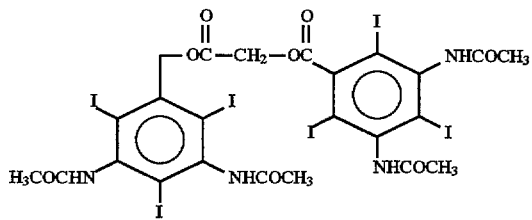

For convenience, the reaction can take place at an ambient pressure, although higher and lower pressures are contemplated. Preferred temperatures are from 0° to 150° C.

The reaction can take place in any suitable solvent. Suitable solvents include, N,N-dimethylformamide (DMF) and dimethylsulfoxide (DMSO).

The iodinated compounds can contain substituents which do not deleteriously affect the contrast-enhancing capability of the compound. For example, the alkyl and aryl groups in structure I above can be unsubstituted or substituted with various substituents which do not adversely affect the stability or efficacy of the compounds as x-ray contrast agents such as alkyl, cycloallcyl, aryl, aralkyl, alkoxy, hydroxy, acyloxy, halogen, such as chlorine, bromine and iodine, acylamino, carboalkoxy, carbamyl and the like.

When used as an x-ray contrast agent, the compound of this invention preferably comprises at least about 30%, more preferably at least 35%, and most preferably at least 40% iodine by weight.

In preferred embodiments, the compounds of this invention can be formulated into particulate x-ray contrast compositions, preferably nanoparticulate x-ray contrast compositions, as described in commonly-owned EP-a 498, 482. Preferred compounds exhibit a melting point of greater than 150° C. Such nanoparticulate compositions can be prepared by dispersing the compounds of the invention in a liquid dispersion medium, and wet grinding the compound in the presence of rigid grinding media and a surface modifier to form the nanoparticles. Alternatively, the surface modifier can be contacted with the compound after attrition. Preferred surface modifiers include nonionic surfactants.

In preferred embodiments, the surface modifier is a high molecular weight nonionic surfactant. Preferred surfactants include poloxamers such as Pluronicä F68 and F108, which are block copolymers of ethylene oxide and propylene oxide, poloxamines, such as Tetronicä 908 (also known as Poloxamine 908), which is a tetrafunctional block copolymer derived from sequential addition of propylene oxide and ethylene oxide to ethylenediamine, and dialkyl esters of sodium sulfosuccinic acid, such as dioctylsulfosuccinate sodium (DOSS). The concentrations of the surface modifier can vary from about 0.1–75%, preferably 1–60%, and more preferably 5–25% by weight based on the total combined weight of the contrast agent and surface modifier.

In preferred embodiments, the x-ray contrast composition in the form of surface modified nanoparticles can be associated with a cloud point modifier to further enhance stability during steam heat antoclaving, i.e., the cloud point modifier can reduce particle aggregation during heat sterilization. Preferred cloud point modifiers include nonionic cloud point modifiers, such as polyethylene glycols such as PEG 400, propylene glycol, ethanol, hydroxypropylcyclodextrin and glycerol; ionic cloud point modifiers, such as those described in U.S. Pat. No. 5,298,262 including dialkylesters of sodium sulfosuccinic acid such as the dioctylester of sodium sulfosuccinic acid (DOSS); and charged phospholipids, such as diacylphosphatidyl glycerol and dimyristoylphosphatidyl glycerol. The cloud point modifier can be present in an amount of 0.005–50%, preferably 0.01–30% and more preferably 0.05–20% by weight based on the total weight of the x-ray contrast composition.

The x-ray contrast compositions of this invention comprise the above-described compounds, preferably in the form of particles, and a physiologically acceptable carrier therefor. For example, the particles can be dispersed in an aqueous liquid which serves as the carrier for the x-ray contrast agent. Other suitable carriers include liquid carriers such as mixed aqueous and nonaqueous solvents, such as alcohol; gels; gases, such as air; and powders.

The x-ray contrast composition can comprise from about 1–99.9, preferably 2–45 and more preferably 10–30% by weight of the above-described particles, the remainder of the composition being the carrier, additives and the like. Compositions up to about 100% by weight of the particles are contemplated when the composition is in a lyophilized form.

The dose of the contrast agent to be administered can be selected according to techniques known to those skilled in the art such that a sufficient contrast enhancing effect is obtained. Typical doses can range from 20 to 450 mg of iodine per kilogram of body weight of the subject for many imaging applications. For some applications, e.g., lymphography, lower doses, e.g., 0.5–20 mg I/kg, can be effective. For blood pool imaging, the dose can range from 50 to 450 mg of iodine per kilogram of body weight and preferably from 100 to 250 mg of iodine per kilogram of body weight. For liver and spleen imaging, the dose can range from 1 to 20 mg/kg.

The x-ray contrast composition can contain one or more conventional additives used to control and/or enhance the properties of the x-ray contrast agent. For example, thickening agents such as dextran or human serum albumin, buffers, viscosity regulating agents, suspending agents, peptizing agents, anti-clotting agents, mixing agents, and other drugs and the like can be added. A partial listing of certain specific additives includes gums, sugars such as dextran, human serum albumin, gelatin, sodium alginate, agar, dextrin, pectin and sodium carboxymethyl cellulose. Such additives, surface active agents, preservatives and the like can be incorporated into the compositions of the invention.

A method for diagnostic imaging for use in medical procedures in accordance with this invention comprises administering to the body of a test subject in need of an x-ray an effective contrast producing amount of the above-described x-ray contrast composition. In addition to human patients, the test subject can include mammalian species such as rabbits, dogs, cats, monkeys, sheep, pigs, horses, bovine animals and the like. Thereafter, at least a portion of the body containing the administered contrast agent is exposed to x-rays to produce an x-ray image pattern corresponding to the presence of the contrast agent. The image pattern can then be visualized. For example, any x-ray visualization technique, preferably, a high contrast technique such as computed tomography, can be applied in a convention manner. Alternatively, the image pattern can be observed directly on an x-ray sensitive phosphor screen-silver halide photographic film combination.

The compositions of this invention can be administered by a variety of routes depending on the type of procedure and the anatomical orientation of this tissue being examined. Suitable administration routes include intravascular (arterial or venous) administration by catheter, intravenous injection, rectal administration, subcutaneous administration, intrathecal administration, intracisternal administration, oral administration, administration via inhalation, administration directly into a body cavity, e.g., arthrography, and the like.

In addition to preferred application, i.e., for blood pool, liver, spleen and lymph node imaging, the x-ray contract compositions of this invention are also expected to be useful as contrast agents for any organ or body cavity. For example, the compositions of this invention are expected to be useful as angiographic contrast media, urographic contrast media, myelographic contrast media, gastrointestinal contrast media, cholecystographic and cholangiographic contrast media, arthrographic contrast media, hysterosalpingographic contrast media, oral contrast media and bronchographic contrast media.

The following examples further illustrate the invention.

EXAMPLE 1

Preparation of Preferred Compound

To a stirred solution of a compound having the structure

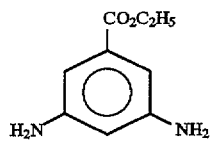

is added a nitrate (NaNO$_3$, KNO$_3$ or CsNO$_3$) to form the compound having the structure

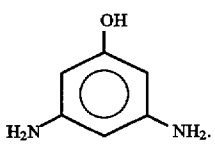

To this product is added 1) Ac$_2$O, 2) 20% KOH/H$_2$O neat and 3) AcOH to provide the compound having the structure

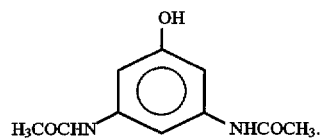

The above product is reacted with NaCl$_2$I (40% in H$_2$O) at a temperature of 40° C. to form the compound

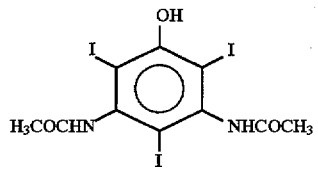

To the above product is added diatrizoic acid, sodium or potassium salt having the structure

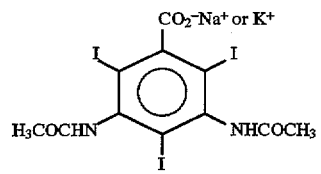

in DMF at a temperature of 30° C. to form the compound having the structure:

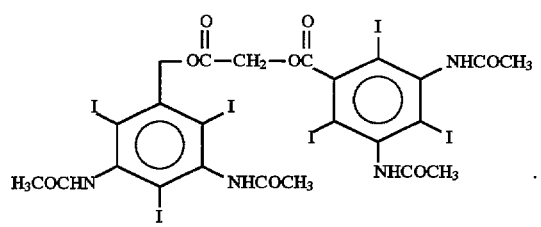

EXAMPLE 2

Preparation of Nanoparticulate Compound 1 Contrast Agent with Pluronic F68, Pluronic F108, or Tetronic T-908

Compound 1, above, is added to each of 3×1.5 oz brown glass bottles containing approximately 12 ml of zirconium silicate (1.1 mm dia.) beads in an amount sufficient to be 15% (w/v) of the final suspension Bottle A contains 3% (w/v) Pluronic F-68. Bottle B contains 3% (w/v) Pluronic F108. Bottle C contains 3% (w/v) Tetronic T-908. The resulting suspensions are milled on a roller mill at approximately 150 rpm for a total of 9 days.

EXAMPLE 3

Preparation of Nanoparticulate Compound 1 Contrast Agent with Pluronic F108 and Blood Pool Imaging 15% Compound 1 can be milled with 4% Pluronic F-108 in the present of zirconium silicate (1.1 mm din) beads for 3 days under aseptic conditions. No additional salts or surfactants are added.

This sample is examined for imaging efficacy. The sample is injected into white New Zealand rabbits at a dose of 3 ml/kg as a slow bolus injection. At times of 5, 15, 30, 60 and 120 min. post injection, the opacification of the liver, spleen, and blood pool as measured in the aorta and within the left ventricle is determined by computed tomography (CT) using a Toshiba 900S Imager CT scanner and associated software. Results from this analysis are expected to show that this formulation of Compound 1 has excellent blood pool opacification in excess of 30 min. followed by very good liver and very good spleen opacification for 120 min. Imaging at 24 hours post injection should show complete clearance from the blood with partial clearance from the liver and spleen.

EXAMPLE 4

Preparation of an Autoclavable Formulation of Nanoparticulate Compound 1 Contrast Agent with Pluronic F108 and PEG 400 and Lymphography Imaging Compound 1 is milled with zirconium silicate (1.1 mm dia) beads in the presence of Pluronic F-108 for 3 days. The final particle size is determined. At this point, sterile PEG 400 is added to the suspension such that at completion, the formulation contains 15% (w/v) WIN 70146, 3% (w/v) Pluronic F-108, and 10% (w/v) PEG 400. This formulation is then autoclaver under standard conditions, i.e., 121° C. for 20 min.

This formulation is evaluated for both blood pool and lymphographic imaging in New Zealand White Rabbits using the above-described protocol (3 ml/kg) for blood pool imaging and 2 injections (0.25 ml) per paw for lymphography. The results should indicate that Compound 1 is capable of blood pool opacification to at least 30 min. and is an excellent lymphography agent affording the highest level of opacification noted to date in this indication. Scanning is carried out using a Toshiba 900S Imager CT scanner and image density is calculated from iodinated standards imaged simultaneously with the animals.

The invention has been described in detail with particular reference to certain preferred embodiments thereof, but it will be understood that variations and modifications can be effected within the spirit and scope of the invention.

We claim:

1. A compound having the structure:

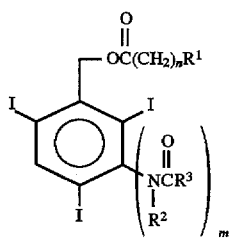

wherein:

n is 0 to 12 m is 1 or 2; $R^1$ is

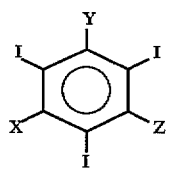

X and Z are independently H or $NR^2COR^3$

Y is $CO_2$, $CH_2O$, O or NH and $R^2$ and $R^3$ are independently H, alkyl having from 1 to 12 carbon atoms or aryl having from 6 to 11 carbon atoms.

2. The compound of claim 1 wherein X and Z are $NHCOCH_3$.

3. The compound of claim 1 wherein $R^1$ is

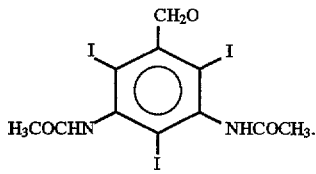

4. The compound of claim 1 wherein $R^1$ is

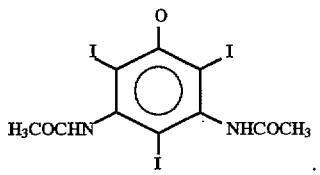

5. A compound having the structure:

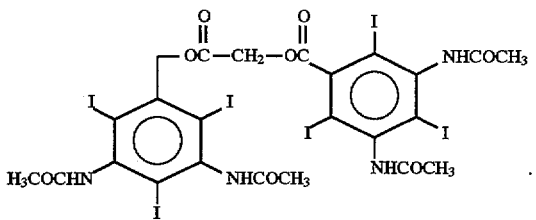

6. A method of reducing x-ray diagnostic imaging the blood pool, liver, spleen or lymph system of a mammal comprising administering to the mammal a contrast effective amount of a 3-amido-triiodophenyl ester having the structure:

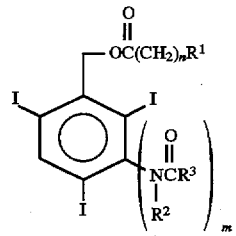

wherein:

n is 0 to 12 m is 1 or 2; $R^1$ is

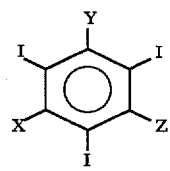

X and Z are independently H or $NR^2COR^3$

Y is $CO_2$, $CH_2O$, O or NH and $R^2$ and $R^3$ are independently H, alkyl having from 1 to 12 carbon atoms or aryl having from 6 to 11 carbon atoms.

7. The method of claim 6 wherein X and Z are NHCOCH₃.

8. The method of claim 6 wherein R¹ is

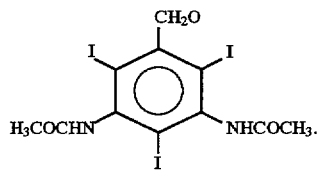

9. The method of claim 6 wherein R¹ is

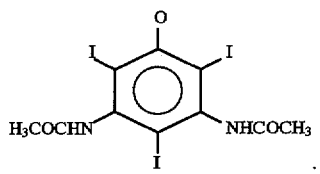

10. The method of claim 6 wherein the compound has the structure

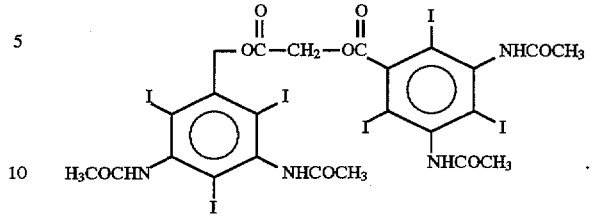

11. An x-ray contrast composition comprising the compound of claim 1.

12. The x-ray contrast composition of claim 11 further including a pharmaceutically acceptable carrier.

13. A method for medical x-ray diagnostic imaging which comprises administering to the body of a mammal a contrast enhancing effective amount of the x-ray contrast composition of claim 12.

* * * * *